United States Patent [19]

Marsh

[11] 4,098,831
[45] Jul. 4, 1978

[54] NITROBENZOTRICHLORIDE OR BROMIDE PROCESS

[75] Inventor: Frank Dennis Marsh, Wilmington, Del.

[73] Assignee: E. I. Du Pont de Nemours and Company, Wilmington, Del.

[21] Appl. No.: 822,998

[22] Filed: Aug. 3, 1977

[51] Int. Cl.$^2$ .............................................. C07C 79/12
[52] U.S. Cl. ................................................... 260/646
[58] Field of Search ......................................... 260/646

[56] References Cited

U.S. PATENT DOCUMENTS

| | | | |
|---|---|---|---|
| 3,267,159 | 8/1966 | Shipp | 260/646 |
| 3,993,704 | 11/1976 | Marsh et al. | 260/646 |

OTHER PUBLICATIONS

Docks, Synthesis, pp. 441 to 456 (1973); Chem. Abs., vol. 79, 125710u (1973).
Dehmlow, Angew. Chem., Int. Ed., vol. 13, pp. 170 to 179 (1974).
Lee et al., Tetrahedron Letters, No. 20, 1641 to 1644 (1976).
Fisher, J. Am. Chem. Soc., vol 56, pp. 2469 to 2470 (1934).

*Primary Examiner*—Leland A. Sebastian
*Attorney, Agent, or Firm*—Anthony P. Mentis

[57] ABSTRACT

In the hypohalite halogenation in a two phase aqueous-/organic solvent medium of a mono- or dichloro- or bromo-methylnitrobenzene to a corresponding trihalomethylnitrobenzene, the improvement wherein the reaction is conducted in the presence of a phase transfer catalyst or where the organic phase is a $C_4$ to $C_8$ alkanol.

10 Claims, No Drawings

NITROBENZOTRICHLORIDE OR BROMIDE PROCESS

BACKGROUND OF THE INVENTION

1. Field of the Invention

A mono- or dichloro- or bromo-methylnitrobenzene is halogenated by a hypohalite in a two phase aqueous-/organic solvent medium in the presence of a phase transfer catalyst or where the organic phase is a $C_4$-$C_8$ alkanol to produce a trichlormethylnitrobenzene.

2. Prior Art

U.S. Pat. No. 3,993,704 shows a two phase aqueous-/organic solvent process for conversion of p-nitrobenzal bromide to p-nitrobenzotribromide by use of a metal hypobromite where the organic phase is a chlorinated aliphatic hydrocarbon such as $CCl_4$, an aromatic hydrocarbon such as toluene or a halogenated aromatic hydrocarbon such as chlorobenzene. The time needed for the reaction or the yields of product are not entirely satisfactory and the process is not operable with a nitrobenzyl bromide or a nitrobenzylchloride.

DESCRIPTION OF THE INVENTION

It has now been found that by the use of a selected organic solvent or a phase transfer catalyst, an improvement in yield or decrease in reaction time is achieved. Also, nitrobenzyl compounds can be used as starting materials.

The invention is the process for the preparation of an o- or p-trihalomethylnitrobenzene by reacting the corresponding mono or dihalomethylnitrobenzene with an alkali metal or alkaline earth hypochlorite or hypobromite or an alkyl hypochlorite or hypobromite wherein the alkyl is of 1–10 carbons under strongly alkaline aqueous conditions in a two phase aqueous/organic solvent system wherein a quaternary ammonium or phosphonium phase transfer catalyst is present in the reaction mixture or the organic phase comprises an alkanol of 4 to 8 carbons.

The invention can be described as the process of reacting, in a two-phase aqueous-organic solvent system in which the aqueous phase contains 7–50% by weight of an alkali metal hydroxide or carbonate, a nitro compound of the formula

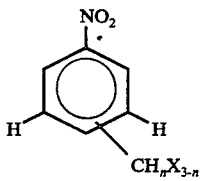

with a compound of the formula ROX to produce a compound of the formula

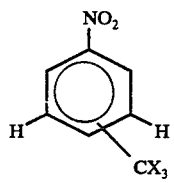

wherein
each X is independently chlorine or bromine;
R is alkali metal, alkaline earth metal or alkyl or cycloalkyl of 1–10 carbons; and
n is 1 or 2,
which comprises carrying out the reaction in the presence of 0.01 to 20% by weight of the starting nitro compound of a quarternary ammonium salt or quaternary phosphonium salt, or carrying out the reaction where the organic solvent system comprises an alkanol of 4–8 carbons.

The reaction may be considered as

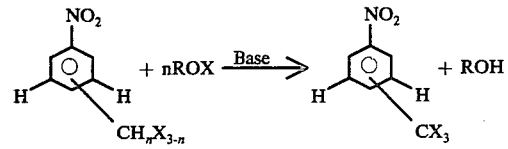

where n, X and R are as previously defined.

The compounds prepared by the process of the invention are α,α,α-trihalonitrotoluenes in which the halogens are chlorine and bromine and are not necessarily the same in one compound. The preferred compounds are those where the trihalomethyl group is in the para position and in which the halide is chlorine. The process thus provides for the complete side chain halogenation of ortho or para nitrobenzylchloride, nitrobenzylbromide, nitrobenzalchloride or nitrobenzalbromide. The process also permits the ready preparation of mixed halides such as α,α-dichloro-α-bromo-p-nitrotoluene or α,α-dibromo-α-chloro-p-nitrotoluene.

The o- or p-mono- or dihalomethylnitrobenzenes useful as starting materials include α-chloro-, α-bromo-, α,α-dichloro-, α,α-dibromo-, α-bromo-α-chloro-, o- and p-nitrotoluenes.

Hypohalites include sodium, potassium, lithium, and calcium hypochlorites and hypobromites. Hypohalites of aliphatic and cycloaliphatic alcohols are those of 1–10 carbons that have 1–2 alcoholic hydroxyls and are hydrocarbon except for hydroxy and include methanol, ethanol, propanol, butanol, tertiary butanol, pentanol, cyclohexanol, hexanol-1, heptanol-1, 3-methyl-3-hexanol, octanol-1, 2,3-dimethyl-3-pentanol and the like. Preferred of the aliphatic hypohalites are the hypochlorites and hypobromites of tertiary alkanols, especially those of 4–6 carbons such as t-butanol, t-pentanol and t-hexanol.

The inorganic alkali and alkaline earth metal hypohalites are articles of commerce or are readily available, e.g., being prepared by action of halogen on an alkaline hydroxide solution. Organic hypohalites are readily obtained by action of chlorine or bromine on an alcohol in the presence of an alkali metal hydroxide, or less preferred, by action of hypochlorous or hypobromous acids on the alcohol. It is preferred that the organic hypohalites be generated in the reaction mixture since isolation and addition of preformed organic hypohalites may introduce a potential explosion hazard.

The agent used to make the aqueous media strongly alkaline is an alkali metal hydroxide or carbonate, e.g., lithium, sodium or potassium hydroxide, or sodium carbonate, etc. Quaternary hydroxides can be used as the alkaline source but sodium or potassium hydroxide are preferred.

Concentration of the alkali hydroxide in water can vary from 7–50% by weight with 25–40% being generally preferred.

The reaction can be carried out at temperatures of 0°–100° C with above 15° generally being used and 25°–45° being preferred. Reaction time can vary from 1 to 24 hours but with phase transfer catalysts the time is generally 0.25 to 2 hours. The exact time depends on the temperature and reactants as well as the media. By the use of phase transfer catalysts or the alkanols the speed of reaction is increased and the time required is shortened considerably over that needed in their absence.

A two phase reaction media is necessary to obtain satisfactory yields and prevent excessive by-product formation. One phase is the aqueous base while the other is an organic solvent in which the α-halonitrotoluene dissolves and which is generally inert to the strong alkali and hypohalite. When using a phase transfer catalyst the organic solvent can include halogenated aliphatics such as chlorinated methanes, ethanes and butanes; hydrocarbons such as cyclohexane, hexane, decane, benzene, toluene, xylene; alcohols having three carbons or more such as t-butanol, pentanol, hexanol, etc. When alcohols of 1–3 carbons are used, a cosolvent such as halogenated hydrocarbon is added since such alcohols as methanol and ethanol are miscible with aqueous alkali and do not form two phases.

The $C_4$ to $C_8$ alkanols include butanol, pentanol, hexanol, heptanol or octanol, and particularly the corresponding tertiary alcohols which have an unusual combination of solvent and nonsolvent properties for the organic reactants and alkali, etc. Particularly preferred are the $C_4$ and $C_5$ alkanols.

The use of phase transfer catalysts (PTC) is particularly preferred since they markedly increase the speed of reaction. They are a recognized class of materials and have been used in alkylation, replacement of halogen by cyanide, carbene reactions, oxidation and reduction or elimination of hydrogen halide in organic compounds [Dehmlow, Angen, Chem. Int. Ed. Eng., 13, 170 (1974)]. They have also been used to oxidize alcohols by aqueous hypochlorite [Lee et al., Tetrahedron Letters, 20, 1641 (1976)] and to effect halogen exchange, e.g., Br for Cl [Docker, Synthesis, 441 (1973)].

The phase transfer catalysts used in this invention are quaternary ammonium or phosphonium salts. They are generally employed as halide salts but under the conditions of basicity used in this reaction, they may be present as the hydroxide. These quaternary compounds are well recognized commercial products and readily available. Usually they are hydrocarbon in nature except for nitrogen, phosphorous and the salt group (which is generally an inorganic ion), although nonreactive groups such as halogen, hydroxy, and alkoxy or other ether linkages can be present. They contain from 4 to 30 carbon atoms in the total molecule. The amount of PTC present is generally 0.01 to 20% by weight or more based on the starting nitrotoluene compound, with 1–10% being preferred.

A quaternary ammonium salt or a quaternary phosphonium salt is a compound where a central nitrogen atom, or a phosphorous atom, is joined to four organic groups, alike or different, as well as to an acid radical of some sort. Exemplary are octadecyldimethylbenzylammonium chloride, tetrabutylammonium bromide, N,N-dimethyl-N-(β-hydroxyethyl)-N-dodecylammonium bromide, decyltrimethylammonium bromide, methylpolyoxyethylene (15) cocoammonium chloride (Ethoquad C/25), benzyltriethylammonium chloride, tetrabutylphosphonium bromide, decyltrimethylphosphonium bromide, dodecyltriethylphosphonium bromide, benzyltrimethylphosphonium chloride, octadecyldimethylbenzylphosphonium chloride and the like.

The total volume of the two phase system per mole of α-halo-nitrotoluene as well as the ratio of organic to aqueous phase may vary widely. In general it is desirable to keep the α-halo-nitrotoluene concentration low to prevent side reactions. This can be conveniently accomplished by adding the starting nitrotoluene compound slowly as a solid or as a concentrated solution to the reaction mixture. Good yields of product can be obtained when the α-halo-nitrotoluene is added in a single portion provided about 1–4 liters of organic phase are used per mole of the α-halo-nitrotoluene. With lower molecular weight alcohols the reaction is more rapid and higher concentrations of the α-halo-nitrotoluene can be used.

The volume ratio of organic phase to aqueous phase can vary from 1:8 to 8:1. The volume of organic phase normally exceeds the aqueous phase and ratios between 1.1 and 4 are normally used, but ratios as high as 5–8 are operable, particularly when a phase transfer catalyst is present. Alternatively the volume of aqueous phase may exceed the organic phase.

A small excess (5–10%) of halogen is frequently used, but not required, to give good yields. Alternatively a slight excess of the α-halo-nitrotoluene may be used. The base is normally used in considerable excess but an equivalent or less may be adequate when phase transfer catalysts are present. Alcohols may be used as solvent and reactant (to form an alkylhypohalite) or may be used in equivalent weight or less in conjunction with a cosolvent.

Under optimum conditions by-products do not normally exceed 1–5% of the reaction product and consist chiefly of nitrobenzoic acid, nitrobenzyl alcohols, and coupled products (stilbene-type products). Long reaction times and high temperatures appear to promote nitrobenzoic acid formation while high concentrations of the α-halo-nitrotoluene or low hypochlorite concentrations increase coupled product formation.

The reaction may be carried out in a batch or continuous process. The hypohalite can be prepared and isolated before it is subsequently reacted with the α-halo-nitrotoluene in the two phase system even though isolation of hypohalite can introduce hazards. The α-halo-nitrotoluene may be dissolved in a suitable solvent and the hypohalite and base added. Alternatively, the α-halo-nitrotoluene may be added as a solid or as a solution in a suitable solvent to the two phase mixture of base, halogen and solvent. The mixture is stirred and heated until the benzyl hydrogens are replaced by halogen. This can be shown by the Hnmr spectra.

In a convenient modification, halogen is added to the two phase mixture of aqueous base and inert organic solvent at 0°–30°. The α-halo-nitrotoluene can then be added as a solid or in a suitable solvent and the reaction mixture heated until the benzyl hydrogens are replaced by halogen. Less by-products are found if the α-halo-nitrotoluene is added slowly as a solid or in a suitable solvent at the reaction temperature.

The α,α,α-trihalonitrotoluenes are products readily isolated by a number of procedures. The organic phase may be separated, dried, and the solvent removed to give essentially pure nitrobenzotrihalide as a white to pale yellow crystalline solid. The water layer may be filtered to remove alkali metal halide and the filtrate recycled. The α,α,α-trihalonitrotoluenes are useful intermediates in the production of p-aminobenzotrifluoride used to prepare the insecticide 1,5-bis(4-trifluoromethylphenyl)-3-cyanoformazan according the the disclosure in U.S. Pat. No. 3,993,704 to Marsh et al.

SPECIFIC EMBODIMENTS OF THE INVENTION

In the following illustrative examples all parts are by weight and all temperatures are degrees Centigrade unless stated otherwise.

EXAMPLE 1

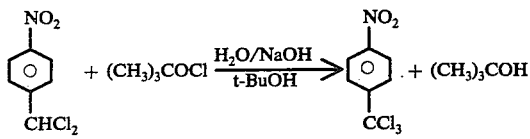

p-Nitrobenzal chloride (p-NBCl$_2$, 3.9 g, 0.0189 mole) in t-butyl alcohol (50 ml) was added to a solution of sodium hydroxide (10 g) in water (50 ml). The two phase mixture was stirred and t-butyl hypochlorite (4.5 g, 0.049 mole) was added. The mixture was stirred and heated at 53°–60° for 17 hr. An aliquot (20 ml) of the reaction mixture was poured onto ice and extracted with methylene chloride. The extract was dried and the methylene chloride removed on a rotary evaporator (1 mm/25°). The Hnmr showed no absorption at 408 cps characteristic of the benzal proton of p-nitrobenzal chloride. After heating an additional 3 hr, the product was isolated in the same manner as the aliquot to give an off-white solid (3.0 g). The product was recrystallized from petroleum ether (bp 39°–50°) to give pure p-nitrobenzotrichloride, mp 46°–47°.

EXAMPLE 2

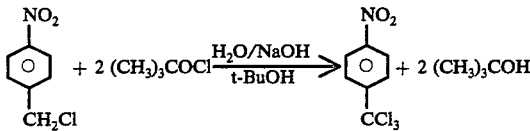

p-Nitrobenzyl chloride (5.0 g, 0.029 mole) in t-butyl alcohol (75 ml) was added to a solution of sodium hydroxide (15 g) in water (50 ml). t-Butylhypochlorite (7.06 g, 0.065 mole) was added and the two phase mixture stirred and heated at 50° for 6 hr. An aliquot (20 ml) was removed, poured onto ice, and extracted with methylene chloride. The Hnmr spectra showed no absorption at 280 cps characteristic of the benzyl protons of p-nitrobenzyl chloride. After heating an additional 16 hr the product was isolated in the same manner as the aliquot to give a pale yellow solid (4.85 g) having spectral properties identical with authentic p-nitrobenzotrichloride.

The water layer was adjusted to pH 1 with hydrochloric acid and filtered to separate p-nitrobenzoic acid (0.5 g).

EXAMPLE 3

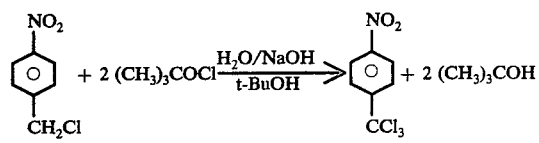

To p-nitrobenzyl chloride (20.0 g, 0.117 mole) dissolved in t-butyl alcohol (400 ml) was added t-butylhypochlorite (27.9 g, 0.232 mole) and then sodium hydroxide (60 g) dissolved in water (200 ml). The mixture was stirred and heated at 47°–54° for 1 hr. The layers were separated and the water layer was extracted with methylene chloride (2 × 150 ml). The organic layers were combined, dried over anhydrous magnesium sulfate and the solvent removed under reduced pressure (1 mm/25°–40°) on a rotary evaporator to give a pale yellow crystalline solid (28.2 g) which was shown by gas liquid chromatography to contain p-nitrobenzotrichloride (93.64%) and unreacted p-nitrobenzyl chloride (3.2%); yield 98.7, conversion 99.5%.

EXAMPLE 4

The procedure described in Example 3 was repeated on a larger scale using slightly less than the theoretical amount of t-butylhypochlorite. From p-nitrobenzyl chloride (142.9 g, 0.83 mole), t-butylhypochlorite (179.0 g, 1.65 mole), sodium hydroxide (214.3 g), water (714 ml) and t-butyl alcohol (1500 ml) was obtained as a pale yellow crystalline solid shown by gas-liquid chromatography to contain p-nitrobenzotrichloride (96.8%) and p-nitrobenzyl chloride (1.8%); yield based on t-butylhypochloride 88.2%, conversion 97.8%.

EXAMPLE 5

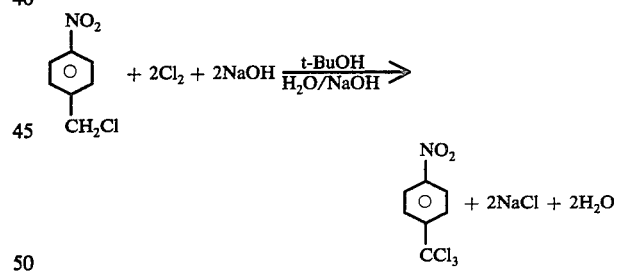

t-Butyl alcohol (654 ml) was added to a sodium hydroxide solution prepared from NaOH (160 g) and water (350 ml). The two phase mixture was cooled at 10°–15°, while chlorine (40 g, 0.56 mole) was added as a gas over the surface during 0.5 hr. p-Nitrobenzyl chloride (40 g, 0.23 mole) was added as a solid and the mixture heated at 45°–52° for 1¼ hr. The layers were separated and the aqueous layer was extracted with methylene chloride (2 × 200 ml). The combined organic extracts were washed with water, dried (MgSO$_4$) and the solvent removed on a rotary evaporator to give a pale yellow crystalline solid which was shown by gas liquid chromatography to consist of p-nitrobenzotrichloride (98.2%) and p-nitrobenzyl chloride (1.0%); yield 81%, conversion 98.7%. The water layer was acidified and filtered to separate p-nitrobenzoic acid (0.2 g).

EXAMPLE 6

The procedure of Example 5 was repeated using p-nitrobenzyl chloride (42.9 g, 0.25 mole) sodium hydroxide (57 g), water (100 ml), t-butyl alcohol (400 ml) and chlorine (39 g, 0.55 mole) and the reaction was stirred and heated at 50°–54° for 1 hr. The layers were separated and the water layer filtered to separate solid (1.45 g). The filtrate was extracted with methylene chloride (2 × 200 ml) and the extract combined with the t-butyl alcohol layer. The combined extracts were dried (MgSO$_4$) and the solvent removed on a rotary evaporator (1 mm/25°–40°) to give a yellow solid (48.95 g). This solid was slurried with ether and filtered to separate a yellow solid (12.95 g) which after recrystallization from toluene melted at 194°–213° and is apparently a stilbene-type compound.

Anal. Calcd for $C_{14}H_{10}N_2O_4Cl_2$: C, 49.29; H, 2.95; N, 8.21; O, 18.76; Cl, 20.78.

| C, 50.35; | H, 2.88; | N, 8.36; | Cl, 18.49 |
|---|---|---|---|
| 50.33 | 2.80 | 8.17 | |

Molecular weight: Calcd: 337.9860. Found: 337.9859 (mass spec.).

The ether was removed from the filtrate to give a pale yellow oil (32.4 g) which contained p-nitrobenzotrichloride (92.1%) and p-nitrobenzyl chloride (4.3%); yield 51.3%, conversion 96.8% as determined by gas-liquid chromatography (g.l.c.).

EXAMPLE 7 t-Butyl alcohol (300 ml) was added to a sodium hydroxide solution prepared from NaOH (70 g) and water (100 ml). The two phase mixture was cooled at 15°–20° while chlorine (42.6 g, 0.6 mole) was added as a gas over the surface during 0.5 hr. The mixture was maintained at 49°–54° and p-nitrobenzyl chloride (42.9 g, 0.25 mole) was added in 5 g portions during 50 minutes. The reaction which is mildly exothermic was maintained at 49°–54° for an additional 40 minutes. The layers were separated and the water layer was extracted with methylene chloride. The extracts were combined with the alcohol layer, dried (MgSO$_4$) and the solvent removed on a rotary evaporator (1 mm/25°–40°) to give pale yellow crystals (55.65 g) which were shown by g.l.c. to consist of p-nitrobenzotrichloride (94.4%) and p-nitrobenzyl chloride (1.7%); yield 89.4%; conversion 98%.

The water layer was acidified and filtered to separate p-nitrobenzoic acid (1.25 g).

When the above general procedure was repeated except that 400 ml of t-butyl alcohol and 0.5 m of chlorine were used, and 4.3 g tetramethylammonium bromide added, p-nitrobenzotrichloride was also obtained in good yield.

EXAMPLE 8

Example 7 was repeated using 30 g of NaOH to give p-nitrobenzotrichloride at somewhat lower yield and conversion.

EXAMPLE 9

Example 7 was repeated using 40 g of NaOH to give p-nitrobenzotrichloride in 75% yield at 97% conversion.

EXAMPLE 10

Example 7 was repeated using a more concentrated alkali solution, sodium hydroxide (100 g), to give p-nitrobenzotrichloride in 64% yield and 99% conversion.

EXAMPLE 11

Example 7 was repeated using t-amyl alcohol (400 ml) in place of t-butyl alcohol and the reaction was run at 50°–60°. p-Nitrobenzotrichloride was obtained in 76.5% yield at 96.4% conversion.

EXAMPLE 12

(a) Chlorine (39 g, 0.55 mole) was added during 35 min over the surface of a well stirred two-phase mixture consisting of methanol (48 g, 60.5 ml), methylene chloride (240 ml), sodium hydroxide (70 g) and water 100 ml) while cooling at 2°–7°. When addition was complete, t-butylammonium bromide (4.03 g) and p-nitrobenzyl chloride (42.9 g) were added and the mixture was heated to 28° at which point an exothermic reaction raised the temperature to 41°. When the exothermic reaction subsided, heating was continued at 41° for a total of 1 hr. The reaction mixture was diluted with water and the organic layer separated. The water layer was extracted with methylene chloride and the combined organic extracts were dried (MgSO$_4$) and the solvent removed on a rotary evaporator (1 mm/25°–40°) to give a pale tan solid 59.1 g. Analysis of the product by g.l.c. showed it contained p-nitrobenzotrichloride (92%) and p-nitrobenzyl chloride (0.5%); yield 91%, conversion 99.3%.

(b) Repetition of the above without the phase transfer catalyst also evolved heat. However, only a small amount of p-nitrobenzotrichloride was formed and 92% of the p-nitrobenzyl chloride was recovered unreacted.

EXAMPLE 13

Example 12 was repeated using ethyl alcohol (87 ml) and methylene chloride (213 ml) as the organic phase except that heating was carried out at 44° C for 2.5 hr. p-Nitrobenzotrichloride was obtained in 41.6% yield at 94.9% conversion.

EXAMPLE 14

Example 12 was repeated using 3,7-dimethyl-1,7-octanediol (200 ml) as the organic phase and t-butylammonium bromide (1.6 g) as catalyst. The product was isolated in the manner described in Example 12 to give p-nitrobenzotrichloride in good yield and 100% conversion as a solution in 3,7-dimethyl-1,7-octanediol.

EXAMPLE 15

Example 12 was repeated using N,N-dimethyl-N-(β-hydroxyethyl)-N-dodecyl ammonium bromide (0.85 g) as catalyst. The product (50.0 g) contained p-nitrobenzyl chloride (50.2%) and p-nitrobenzotrichloride (44.6%; yield 89.2%; conversion 41.6%) as determined by g.l.c.

EXAMPLE 16

Example 12 was repeated using decyltrimethylammonium bromide (0.7 g) as catalyst. The product (44.8 g) contained p-nitrobenzyl chloride (48.3%) and p-nitrobenzotrichloride (39.3%; yield 57.9%, conversion 49.6%).

the bromine was complete, the mixture was warmed to 30° and p-nitrobenzal chloride (5 g) was added as a solid during 20 minutes with a reaction temperature of 48°–54°. Heating was continued at this temperature for 1 hr after addition was complete. The mixture was diluted with water and filtered to separate a tan powder (15.6 g). The layers of the filtrate were separated and the water layer extracted with methylene chloride. The combined organic layers were dried and the solvent removed on a rotary evaporator to give a solid (8.4 g). This solid was slurried with ether and filtered to separate additional tan solid (1.4 g). The ether was removed on a rotary evaporator to give a light brown oil. This material was sublimed (~80°/0.1 μ) and the sublimate crystallized from petroleum ether (bp 35–55) to give α-bromo-α,α-dichloro-p-nitrotoluene, mp 51.3°–52.9°.

Anal. Calcd for $C_7H_4NO_2Cl_2Br$: C, 29.51; H, 1.42; N, 4.92; $O_2$, 11.23; Cl, 24.89; Br, 28.04 Found:

| C, 29.55; | H, 1.71; | N, 4.78; | Cl, 23.99; | Br, 27.69 |
|---|---|---|---|---|
| 29.87 | 1.79 | '4.91 | | |

Mass spectrometric pattern

| Measured | Calcd for | Assignment |
|---|---|---|
| 247.9119 | 247.9114 | $C_7H_4O_2NClBr$ |
| 203.9622 | 203.9619 | $C_7H_4O_2NCl_2$ |
| 157.9694 | 157.9690 | $C_7H_4Cl_2$ |

Infrared $\gamma_{max}^{KBr}$ 3.20 μ (=CH); 6.20 μ (aromatic C=C); 6.58 μ, 7.42 μ ($NO_2$), 11.94 μ (p-substituted aromatic)

Proton Magnetic Spectra $\delta_{CDCl_3}^{TMSi}$ 8.10 AB quartet

EXAMPLE 24

Example 12 was repeated using p-nitrobenzyl bromide (54.0 g, 0.25 mole) in place of p-nitrobenzyl chloride. Hnmr analysis of the product (37.2 g) isolated from the organic extract showed it to consist of α,α-dichloro-α-bromo-p-nitrotoluene, with small amounts of unreacted p-nitrobenzyl bromide and p-nitrobenzyl alcohol. Acidification of the water layer gave p-nitrobenzoic acid (20.4 g).

EXAMPLE 25

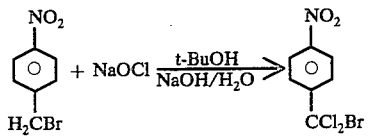

p-Nitrobenzyl bromide (5.25 g, 0.243 mole) in t-butyl alcohol (90 ml) was added to a solution prepared by dissolving sodium hydroxide (14 g) in water (60 ml) and then adding aqueous sodium hypochlorite (5%, 80 ml). The mixture was stirred and heated at 47° for 1 hr and then at ambient temperature for 16 hr. The layers were separated and the water layer extracted with ether. The combined organic extracts were combined and filtered to separate a yellow solid (0.15 g). The filtrate was dried and evaporated to dryness to give a pale tan solid (4.0 g). Hnmr analysis of the product indicated nearly complete conversion of nitrobenzyl bromide to a mixture of α,α-dichloro-α-bromo-p-nitrotoluene and stilbenes. Gas liquid phase chromatographic analysis indicated the presence of p-nitrobenzyl bromide (13.8%) and α,α-dichloro-α-bromo-p-nitrotoluene (51%).

EXAMPLE 26

(a) To a solution of 16 g (0.2 mole) of 50% sodium hydroxide in 100 ml of water, kept at 20°, was added, portionwise, 8 g (0.05 mole) of bromine. The solution was heated to 50° and 1.09 g (0.00339 mole) of tetrabutylammonium bromide was added, followed immediately by a solution of 10 g (0.0339 mole) of p-nitrobenzal bromide in 50 g of toluene. The mixture was stirred at 50° for 1.5 hrs.

The layers were separated, the aqueous layer extracted with 50 g of toluene, and the combined toluene extracts dried ($MgSO_4$), filtered, and evaporated in vacuum to an oil, which turned to a yellow solid. The solid was further dried in a vacuum oven at 40°, affording 11.42 g (90%) of p-nitrobenzotribromide, mp 84°–86°.

(b) This is contrasted to Example 2 of U.S. Pat. No. 3,993,704 wherein similar conditions were used except no PTC (tetraalkylammonium bromide) was present and 10 hrs was required to give an 85% yield.

EXAMPLE 27

To a solution of 3.28 g (0.0820 mole) of sodium hydroxide in 9.84 ml of water, was added 25 ml of toluene and 1.09 g (0.00339 mole) of tetrabutylammonium bromide. The mixture was kept at 15°–25° while 1.91 ml (0.0373 mole) of bromine was added. A solution of 10 g (0.0339 mole) of p-nitrobenzal bromide in 117 ml of toluene was added, and the mixture heated to 55° and kept at 45°–55° for 30 minutes.

The layers were separated, the organic layer washed with water, and the aqueous layer washed with toluene. The combined toluene extracts were dried ($MgSO_4$), filtered, and evaporated in vacuum to a yellow solid. Further drying in a vacuum oven at 40° provided 12.31 g (97%) of p-nitrobenzotribromide, mp 84°–86°.

EXAMPLE 28

Into a stirred, cooled ($\leq 30°$) mixture of 88 g (1.1 moles) of 50% sodium hydroxide and 150 ml of n-butyl chloride, was dripped 25 ml (0.55 mole) of chlorine. After a few minutes, 4.03 g (0.0125 mole) of tetrabutylammonium bromide was added, the thick mixture becoming thinner. After a few more minutes a solution of 10 g (0.05828 mole) of p-nitrobenzyl chloride in 150 ml of n-butyl chloride was added over a 3-minute period. The temperature was kept from rising over 34° during the exothermic reaction which quickly began.

After 1 hour the temperature had fallen to 27° and the n-butyl chloride layer was poured from a thick white paste; the paste was extracted twice with n-butyl chloride. The combined n-butyl chloride solutions were washed with warm water, dried ($MgSO_4$), filtered and evaporated in vacuum to afford a yellow oil, which turned to a yellow crystalline solid, 7.70 g (55% yield); mp 47°–50° of p-nitrobenzotrichloride.

When this experiment is repeated without the tetrabutylammonium bromide the reaction does not occur.

I claim:

1. The process of reacting, in a two-phase aqueous-organic solvent system in which the aqueous phase contains 7–50% by weight of an alkali metal hydroxide or carbonate, a nitro compound of the formula

EXAMPLE 17

Example 12 was repeated except that 300 ml of t-butanol was used as the organic phase and Ethoquad ® c/25 (4.0 g, methylyolyoxyethylene (15) cocoammonium chloride 95% activity; Armak Chemical Division of the Akzona Co.) was used as phase transfer catalyst. The product (40.35 g) contained p-nitrobenzotrichloride 95.4% (yield 64%, conversion 100%).

EXAMPLE 18

Example 12 was repeated using Ethoquad ® c/25 (4.0 g, methyloyloxyethylene (15) cocoammonium chloride 95% active) as catalyst. The product (56 g) contained p-nitrobenzyl chloride (19.3%) and p-nitrobenzotrichloride (69.8%); yield 87.2%, conversion 74.8% as determined by g.l.c.

EXAMPLE 19

Example 12 was repeated using benzyltriethylammonium chloride (1.14 g) as catalyst. The product (47.05 g) contained p-nitrobenzyl chloride (55.9%) and p-nitrobenzotrichloride (30.4%); yield 60.8%, conversion 38.8% as determined by g.l.c. analysis.

EXAMPLE 20

Example 12 was repeated using tetrabutylphosphonium bromide (4.03 g) as catalyst. The product (45.3 g) was slurried with ether and filtered to remove a yellow solid (8.0 g). The solvent was removed from the filtrate on a rotary evaporator to give a solid (36.1 g) containing p-nitrobenzyl chloride (50.3%) and p-nitrobenzotrichloride (11.7%); yield 12.5%, conversion 42.4% as determined by g.l.c. analysis.

EXAMPLE 21

$$\text{o-NO}_2\text{-C}_6\text{H}_4\text{-CH}_2\text{Cl} + \text{Cl}_2 + \text{NaOH} \xrightarrow[\text{H}_2\text{O/NaOH}]{\text{t-BuOH}}$$

$$\text{o-NO}_2\text{-C}_6\text{H}_4\text{-CCl}_3 + \text{o-NO}_2\text{-C}_6\text{H}_4\text{-CHCl}_2 + \text{NaCl} + \text{H}_2\text{O}$$

Example 6 was repeated using o-nitrobenzyl chloride (42.9 g, 0.25 mole) in place of p-nitrobenzyl chloride. The reaction was stirred and heated 1.5 hr at 45°–53°. The product, a brown mobile oil (45.4 g), was distilled in a short path still to give a nearly colorless oil ($n_D^{20.5}$ 1.5772; bath temp. 68°–70°/0.2 μ). Mass spectrometric analysis of the product showed it consisted predominantly of o-nitrobenzal chloride but with some o-nitrobenzotrichloride (the latter identified by g.c. analysis).

| Mass Measured | Calcd | Assignment |
|---|---|---|
| 203.9585 | 203.9619 | $C_7H_4O_2NCl_2$ |
| 170.0027 | 170.0008 | $C_7H_5O_2NCl$ |
| 134.0260 | 134.0242 | $C_7H_4O_2N$ |

An aliquot of the distillate was crystallized twice from carbon tetrachloride-petroleum ether to give pure o-nitrobenzal chloride, mp 25.6°–26.7°.

Anal. Calcd for $C_7H_5NO_2Cl_2$: C, 40.81; H, 2.45; O, 15.53; N, 6.80; Cl, 34.42 Found:

| C, 40.97; | H, 2.81; | N, 6.76; | Cl, 34.20 |
|---|---|---|---|
| 41.21 | 2.65 | 6.84 | |

Infrared Spectrum $\gamma^{liquid}$ 3.52 μ (=CH); 6.18 μ, 6.28 μ and 6.73 μ (aromatic >C=C<); 6.51 μ and 7.40 μ (—NO$_2$)

Proton magnetic spectra $\delta_{CDCl_3}^{TMSi}$ complex group 7.3–8.2

Mass spectrometric analysis

| Measured m/e | Calcd | Assignment |
|---|---|---|
| 204.9686 | 204.9697 | $C_7H_5O_2NCl_2$ |
| 170.0004 | 170.008 | $C_7H_5O_2NCl$ |

In the above example use of o-nitrobenzal chloride instead of o-nitrobenzyl chloride also gives o-nitrobenzotrichloride.

EXAMPLE 22

$$\text{p-NO}_2\text{-C}_6\text{H}_4\text{-CHBr}_2 + \text{ROBr} \xrightarrow[\text{H}_2\text{O/NaOH}]{\text{t-BUOH}} \text{p-NO}_2\text{-C}_6\text{H}_4\text{-CBr}_3 + \text{ROH}$$

Bromine (14.5 g, 0.18 mole) was added dropwise to a well stirred two-phase mixture consisting of sodium hydroxide (23.8 g) water (33.9 ml) and t-butyl alcohol (200 ml) at 10°–20°. When addition was complete, the mixture was heated to 45° and p-nitrobenzal bromide (25 g, 0.085 mole) was added as a solid during 30 minutes with a reaction temp. of 45°–51°. This temperature was maintained for 1 hr after addition was complete. The phases were separated and the water layer extracted with methylene chloride. The combined organic layers were dried and the solvent removed on a rotary evaporator to give a white solid (34.4 g). Analysis of the product by Hnmr showed it contained t-butyl alcohol (27.4%) and p-nitrobenzotribromide (72.6%); yield 78.8%, conversion 100%.

An aliquot of the product was recrystallized from carbon tetrachloride-petroleum ether and then sublimed (~80°/0.2 μ) to give pure p-nitrobenzotribromide mp 86°–87°.

Repetition of this example using o-nitrobenzal bromide gives o-nitrobenzotribromide.

EXAMPLE 23

$$\text{p-NO}_2\text{-C}_6\text{H}_4\text{-CHCl}_2 + \text{Br}_2 + \text{NaOH} \xrightarrow[\text{H}_2\text{O/NaOH}]{\text{t-BuOH}}$$

$$\text{p-NO}_2\text{-C}_6\text{H}_4\text{-CCl}_2\text{Br} + \text{NaBr} + \text{H}_2\text{O}$$

Bromine (19 g, 0.12 mole) was added dropwise to a two-phase mixture consisting of sodium hydroxide (70 g), water (100 ml), t-butyl alcohol (400 ml) with stirring and cooling to maintain 18°–20° C. When addition of

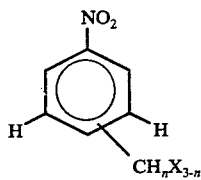

with a compound of the formula ROX to produce a compound of the formula

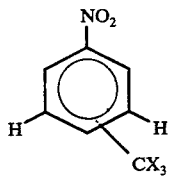

wherein
 each X is independently chlorine or bromine;
 R is alkali metal, alkaline earth metal or alkyl or cycloalkyl of 1–10 carbons; and
 $n$ is 1 or 2, which comprises carrying out the reaction in the presence of 0.01 to 20% by weight of the starting nitro compound of a quartenary ammonium salt or quaternary phosphonium salt, or carrying out the reaction where the organic solvent system comprises an alkanol of 4–8 carbons.

2. The process of claim 1 carried out in the presence of a quaternary ammonium or phosphonium salt.

3. The process of claim 1 carried out where the organic solvent system comprises an alkanol of 4–8 carbons.

4. The process of claim 3 where the alkanol is tertiary butanol.

5. The process of claim 2 using a quaternary ammonium salt.

6. The process of claim 5 using tetrabutylammonium bromide.

7. The process of claim 1 where ROX is t-butyl hypochlorite and the alkali metal hydroxide is NaOH.

8. The process of claim 1 where ROX is t-butyl hypobromite and the alkali metal hydroxide is NaOH.

9. The process of claim 5 using NaOCl.

10. The process of claim 5 using NaOBr.